United States Patent
Yamase et al.

(10) Patent No.: US 6,696,612 B2
(45) Date of Patent: Feb. 24, 2004

(54) PROCESS FOR PRODUCING ISOBUTYLENE AND METHANOL

(75) Inventors: Masanobu Yamase, Ichihara (JP); Yoshiaki Suzuki, Sodegaura (JP); Takayuki Moritou, Niihama (JP)

(73) Assignee: Sumitomo Chemical Company, Limited, Osaka (JP)

( * ) Notice: Subject to any disclaimer, the term of this patent is extended or adjusted under 35 U.S.C. 154(b) by 124 days.

(21) Appl. No.: 10/173,419

(22) Filed: Jun. 18, 2002

(65) Prior Publication Data

US 2003/0009063 A1 Jan. 9, 2003

(30) Foreign Application Priority Data

Jun. 21, 2001 (JP) ........................ 2001-187924

(51) Int. Cl.[7] .................... C07C 33/02; C07C 1/00
(52) U.S. Cl. .................... 568/908; 585/639
(58) Field of Search .................... 568/907, 908 A; 585/324, 639, 647, 651

(56) References Cited

U.S. PATENT DOCUMENTS

| | | |
|---|---|---|
| 3,637,889 A | 1/1972 | Watanabe et al. |
| 4,232,177 A | 11/1980 | Smith, Jr. |
| 4,544,776 A | 10/1985 | Osterburg et al. |
| 5,231,234 A | 7/1993 | Arganbright et al. |
| 6,072,095 A | 6/2000 | Marion et al. |

FOREIGN PATENT DOCUMENTS

| | | |
|---|---|---|
| EP | 0 068 785 A1 | 1/1983 |
| EP | 0 466 954 A1 | 1/1992 |
| EP | 1 149 814 A1 | 10/2001 |
| GB | 1165479 | 10/1969 |
| GB | 1173128 | 12/1969 |
| GB | 1176620 | 1/1970 |
| GB | 1272585 | 5/1972 |
| GB | 2 025 454 A | 1/1980 |
| JP | 47-41882 | 10/1972 |
| JP | 3-45053 B2 | 7/1991 |

OTHER PUBLICATIONS

Derwent Abstract Accession No. 94–046260/06 (SC Carom SA) & RO 105954–B1, (1993).

*Primary Examiner*—Samuel Barts
*Assistant Examiner*—Elvis O. Price
(74) *Attorney, Agent, or Firm*—Sughrue Mion, PLLC

(57) ABSTRACT

A process for producing isobutylene and methanol, comprising decomposing methyl-tert-butylether into isobutylene and methanol, and separating into isobutylene and methanol, thereby individually recovering isobutylene and methanol, the process comprising the following steps:

a first step of subjecting methyl-tert-butylether to decomposition in the presence of a solid acid catalyst;

a second step of washing the resultant with water to separate into an oil layer and a water layer;

a third step of subjecting the oil layer to distillation to obtain a fraction from the top of the distillation column and a fraction from the bottom thereof; and a fourth step of subjecting the water layer to distillation to obtain a fraction containing methanol from the top of the distillation column, a fraction containing water from the bottom thereof and a fraction rich in tert-butanol from a side cut thereof, and then recycling a part or whole of the fraction from the side cut to the first step.

3 Claims, 1 Drawing Sheet

PROCESS FOR PRODUCING ISOBUTYLENE AND METHANOL

BACKGROUND OF THE INVENTION

1. Technical Field

The present invention relates to a process for producing isobutylene and methanol. Particularly, the present invention relates to a process for producing isobutylene and methanol, in which methyl-tert-butyl ether is decomposed into isobutylene and methanol, isobutylene and methanol thus obtained are separated respectively thereby recovering isobutylene and methanol individually, the process being capable of suppressing contamination of methanol as an objective product, with water and tert-butanol and preventing losses of methanol and isobutylene.

2. Description of Related Arts

Methods of recovering isobutylene and methanol by decomposing methyl-tert-butyl ether into isobutylene and methanol and separating isobutylene and methanol respectively therefrom are known (e.g. JP47-041882B).

Further, U.S. Pat. No. 4,544,776 discloses that, in the case of etherifying $C_4$–$C_7$ iso-olefins with methanol, the etherification product(for example, methyl-tert-butyl ether) containing alcohol components such as methanol and a tertiary alcohol (e.g. tert-butanol) is extracted with an excess of water utilizing a washing column directly connected to the reactor as an aqueous extract; when the aqueous extract is distilled utilizing a distillation column, a tert-butanol-water binary azeotrope is taken overhead in this column and thus undesirably increases the water content in methanol to be recover; and when this methanol is reused for etherification, the water contained increases the formation of tert-butanol and thus the increase ultimately results in an additional "snowball effect". As a solution to the above problem, the patent discloses a process wherein an alcohol component is extracted using an excessive amount of water so that a ratio of methanol/water to be extracted becomes 1:2 to 1:5, then the aqueous extract thus obtained is distilled to recover methanol from the top of the distillation column and a highly concentrated tert-alcohol is drawn as a side-stream to be retuned to the washing tower. However, the above process is non-economical since the ratio of water is excessively high, and the process has a drawback that tert-butanol formed by the etherification reaction is ultimately contained in product methyl-tert-butyl ether as one of impurities.

In addition, in a process of recovering isobutylene and methanol by decomposing methyl-tert-butyl ether into isobutylene and methanol and separating isobutylene and methanol respectively therefrom, tert-butanol is also usually contained in methyl-tert-butyl ether as a raw material, in an amount of 0.2 to 0.8 wt %. Depending on a decomposition ratio of methyl-tert-butyl ether, though 50 to 80% of tert-butanol is usually decomposed into isobutylene and water in the first step, undecomposed tert-butanol is distilled from the top of the distillation column in the methanol recovery step due to the residual tert-butanol, to thereby cause a problem that a water content in methanol is increased due to the azeotropy of tert-butanol and water.

SUMMARY OF THE INVENTION

An object of the present invention is to provide a process for producing isobutylene and methanol, wherein isobutylene and methanol are recovered by decomposing methyl-tert-butyl ether into isobutylene and methanol to obtain a mixture thereof, and separating isobutylene and methanol therefrom, the process being capable of suppressing a contamination of methanol as an objective product with both of water and tert-butanol and preventing from losses of isobutylene and methanol.

Namely, the present invention relates to a process for producing isobutylene and methanol comprising decomposing methyl-tert-butyl ether into isobutylene and methanol to obtain a mixture containing isobutylene and methanol, separating isobutylene and methanol respectively therefrom, thereby individually recovering isobutylene and methanol, the process comprising the following steps:

a first step of subjecting methyl-tert-butyl ether to decomposition in the presence of a solid acid catalyst to obtain a reaction liquid containing isobutylene, methanol, and, as by-products, a dialkyl ether and heavy components containing an isobutylene dimer and an isobutylene trimer;

a second step of washing the reaction liquid obtained in the first step with water to separate the reaction liquid into an oil layer and a water layer;

a third step of subjecting the oil layer obtained in the second step to distillation using a distillation column to obtain a fraction containing isobutylene and the dialkylether from the top of the distillation column and a fraction containing methyl-tert-butyl ether and the heavy components from the bottom of the distillation column; and a fourth step of subjecting the water layer obtained in the second step to distillation using a distillation column to obtain a fraction containing methanol from the top of the distillation column, a fraction containing water from the bottom of the distillation column and a fraction rich in tert-butanol from a side cut of the distillation column, and then recycling at least a part of the fraction obtained from the side cut to the first step.

EXPLANATION OF SYMBOLS

Figure 1:
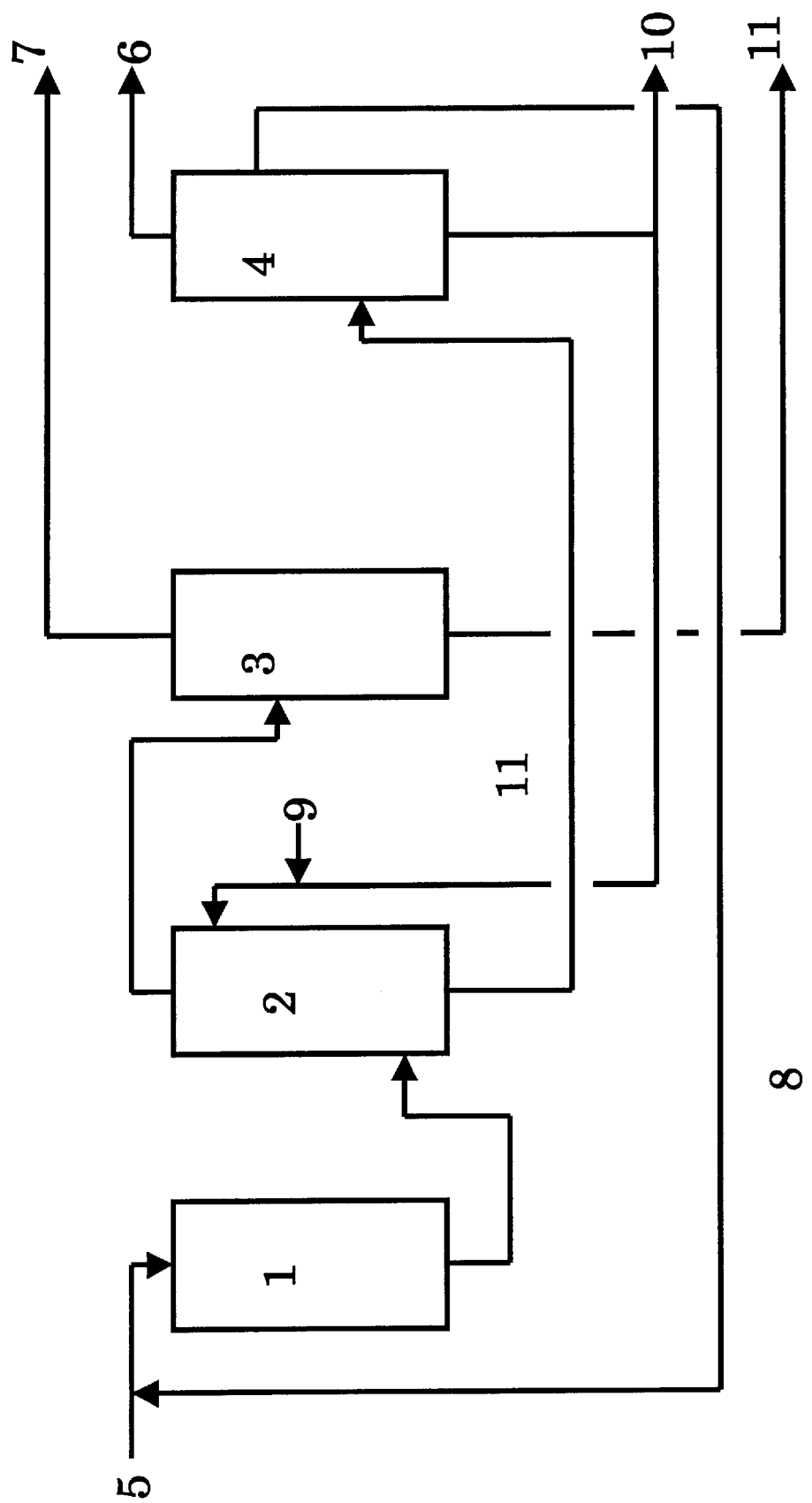
FIG. 1 shows a flow of an example of a production process according to the present invention.

1. First step, 2. Second step, 3. Third step, 4. Fourth step, 5. Methyl tertiary butyl ether (raw material for decomposition), 6. Methanol (objective product), 7. Isobutylene (objective product), 8. Side cut, 9. Freshwater, 10. Wastewater, 11. Waste oil

DETAILED DESCRIPTION OF THE INVENTION

A first step of the present invention is a step of subjecting methyl-tert-butyl ether to a decomposition reaction in the presence of a solid acid catalyst to obtain isobutylene, methanol and a dialkylether and heavy components containing an isobutylene dimer and an isobutylene trimer. Conditions and specific examples of the first step include the followings.

In the first step, a solid acid catalyst, for example, an alumina-modified silica is usually used. A gas phase reaction of a fixed bed is usually adopted in the first step, the reaction temperature is usually from 150 to 300° C. and the reaction pressure is usually from an ordinary pressure to 10 kg/cm$^2$G. A feed rate of a raw material is selected depending on the reaction temperature, reaction pressure, conversion of desired methyl-tert-butylether or the like, and usually from 3 to 20 (h$^{-1}$) in terms of liquid hourly space velocity (LHSV). The reaction gas is liquefied after cooled in a heat recovery equipment.

In a second step, the reaction liquid obtained in the first step is washed with water and then separated into an oil layer and a water layer. Conditions and specific examples of the second step include the followings.

In the second step, any types of extraction column such as a sieve tray type tower and a rotary disk type column can be used. The operation pressure is usually from 6 to 8 kg/cm$^2$G since the reaction liquid is treated in liquid phase. The weight ratio of the washing water/oil is usually from about 0.4 to 0.8, preferably from 0.4 to 0.6 (ratio of methanol/water is 1 : 1.5. In addition, a part or whole of water withdrawn from the bottom of the column in a fourth step is recovered to be reused as the washing water.

In a third step, the oil layer obtained in the second step is subjected to distillation to obtain a fraction containing isobutylene and a dialkylether from the top of a distillation column and a fraction containing methyl-tert-butyl ether and heavy components from the bottom of the distillation column. Conditions and specific examples of the third step include the followings.

A usual distillation column such as a sieve tray type column, a valve tray type column or a packed column can be used in the third step. The operation pressure is a pressure enough to condense a fraction from the top of the distillation column at a temperature of a cooling water generally used, and preferably from 4 to 6 kg/cm$^2$G.

In the fourth step, the water layer obtained in the second step is subjected to distillation to obtain a fraction containing methanol from the top of a distillation column, a fraction containing water from the bottom of the distillation column and a fraction rich in tert -butanol from a side cut of the distillation column, and at least a part of the fraction obtained from the side cut is recycled to the first step. Conditions and specific examples of the present step include the followings.

A usual distillation column such as a sieve tray type column, a valve tray type column and a packed column can be used in the fourth step.

An operation pressure is usually from an atmospheric pressure to 0.3 kg/cm$^2$G. The side cut is a plate in which a concentration of tert-butanol is the highest and usually selected from any of twenty-eighth to thirtieth plate in theoretical plate number from the top of the distillation column. The amount of extracted from the side cut is adjusted so that the amount of tert-butanol contained in the side cut fraction becomes equal to that of tert-butanol fed into the fourth step. In addition, the ratio of methanol/tert-butanol/water contained in the side cut fraction is usually about 80:about 15:about 5, and the whole or a part of the fraction obtained from the side cut may be recycled to the first step.

The most significant characteristic of the process of the present invention is to obtain the fraction rich in tert-butanol from the side cut of the distillation column and to recycle at least a part of the fraction obtained from the side cut to the first step. By adopting the process of the present invention, a methanol product that is substantially free from water and tert-butanol, is obtained from the top of the distillation column, a loss of methanol contained in the side cut fraction is prevented, and the amount of isobutylene obtained by the decomposition of tert-butanol can be increased.

In other words, in the case where the side cut is not taken out, tert-butanol is accumulated in the distillation column and then distilled, and the accumulation of tert-butanol has a function of bringing water to be distilled from the top of the distillation column, thereby increasing water content in methanol.

EXAMPLE

Example 1 and Comparative Example 1

As shown in a flow of FIG. 1, the following first to fourth steps were employed.

But, in Comparative Example 1, a withdrawal of a fraction rich in tert-butanol from a side cut fraction was not conducted in the fourth step. Results in Comparative Example 1 are shown in the following tables. Numerical values in the tables mean wt %.

Abbreviations in the tables are as follows:

MTBE: methyl-tert-butyl ether;

DIB: isobutylene dimer;

DME: dialkyl ether; and

TBA: tert-butanol.

First Step: Methyl-tert-butyl ether was subjected to a decomposition reaction in the presence of an aluminum-containing solid acid catalyst to obtain isobutylene, methanol, by-product dialkylether as well as heavy gravity components including an isobutylene dimer and an isobutylene trimer. A fixed bed gaseous phase reaction was employed. The reaction temperature was 220° C., and the reaction pressure was 6 kg/cm$^2$G. The feed rate of the raw material (feedstock) was 3 (h$^{-1}$) at LHSV base. The reaction gas was liquefied after cooled by a heat recovery equipment.

Second Step: The reaction liquid obtained by the first step was washed with water to be separated into an oil layer and a water layer. A sieve tray type column was employed for the washing, wherein an operation pressure was 7 kg/cm$^2$G at a top of the tower and a weight ratio of the washing water/oil was 0.45.

Third Step: The oil layer obtained by the second step was subjected to a distillation to obtain a fraction consisting of isobutylene and dialkylether from a top of a distillation column as well as a fraction consisting of methyl-tert-butyl ether and heavy components from a bottom of the distillation column. A valve tray type column was used for the distillation, wherein an operation pressure was 5 kg/cm$^2$G.

Fourth Step: The water layer obtained by the second step was subjected to a distillation to obtain a fraction consisting of methanol from a top of a distillation column as well as a fraction consisting of water from a bottom of the distillation column. Whole of the fraction obtained from the side cut was recycled to the first step. A valve tray type column was employed for the distillation, wherein an operation pressure was 0.25 kg/cm$^2$G.

TABLE 1

| | First Step | |
|---|---|---|
| | Feed | Reaction Effluent |
| MTBE | 95 | 4.3 |
| DIB | 0.7 | 0.9 |
| Water | 2.9 | 3.1 |
| Isobutylene | 0.0 | 57.9 |
| Methanol | 0.1 | 32.8 |
| DME | 0.0 | 0.2 |
| TBA | 0.8 | 0.2 |

TABLE 2

Second Step

| | Oil layer after washing | Water layer after washing |
|---|---|---|
| MTBE | 6.3 | 0.4 |
| DIB | 1.5 | 0.0 |
| Water | 0.1 | 60.0 |
| Isobutylene | 90.9 | 0.8 |
| Methanol | 0.0 | 38.6 |
| DME | 0.3 | 0.0 |
| TBA | 0.0 | 0.3 |

TABLE 3

Third Step

| | Effluent from top of column | Effluent from bottom of column |
|---|---|---|
| MTBE | 0.0 | 73.0 |
| DIB | 0.0 | 17.3 |
| Water | 0.1 | 0.0 |
| Isobutylene | 99.5 | 0.1 |
| Methanol | 0.0 | 0.0 |
| DME | 0.3 | 0.0 |
| TBA | 0.0 | 0.0 |

TABLE 4

Fourth Step

| | Effluent from top of column | Effluent from bottom of column |
|---|---|---|
| MTBE | 1.0 | 0.0 |
| DIB | 0.0 | 0.0 |
| Water | 0.1 | 99.7 |
| Isobutylene | 1.9 | 0.0 |
| Methanol | 96.9 | 0.3 |
| DME | 0.0 | 0.0 |
| TBA | 0.7 | 0.0 |

Example 1 was conducted according to the first to fourth steps mentioned above, namely, was conducted in the same manner as in the Comparative Example 1 except for conducting the withdrawal of the fraction rich in tert-butanol from the side cut fraction in the fourth step.

The whole of the fraction was recycled to the first step. A water content in methanol as product was 500 wt ppm or less, and a tert-butanol content was 100 wt ppm or less. A loss of methanol was prevented by 5%, and an amount of isobutylene obtained by tert-butanol recycled to the first step was improved by 0.3%.

As described above, the present invention provides a process for producing isobutylene and methanol by decomposing methyl-tert-butyl ether and separating isobutylene and methanol from methyl-tert-butylether to recover isobutylene and methanol, wherein contamination of methanol, which is a target product, with water and tert-butanol is suppressed as well as losses of isobutylene and methanol are prevented.

What is claimed is:

1. A process for producing isobutylene and methanol comprising decomposing methyl-tert-butyl ether into isobutylene and methanol to obtain a mixture containing isobutylene and methanol, separating isobutylene and methanol respectively therefrom, thereby individually recovering isobutylene and methanol, the process comprising the following steps:

a first step of subjecting methyl-tert-butyl ether to decomposition in the presence of a solid acid catalyst to obtain a reaction liquid containing isobutylene, methanol and, as by-products, a dialkyl ether and heavy components containing an isobutylene dimer and an isobutylene trimer;

a second step of washing the reaction liquid obtained in the first step with water to separate the reaction liquid into an oil layer and a water layer;

a third step of subjecting the oil layer obtained in the second step to distillation using a distillation column to obtain a fraction containing isobutylene and the dialkylether from the top of the distillation column and a fraction containing methyl-tert-butyl ether and the heavy components from the bottom of the distillation column; and a fourth step of subjecting the water layer obtained in the second step to distillation using a distillation column to obtain a fraction containing methanol from the top of the distillation column, a fraction containing water from the bottom of the distillation column and a fraction rich in tert-butanol from a side cut of the distillation column, and then recycling at least a part of the fraction obtained from the side cut to the first step.

2. The process according to claim 1, wherein the amount withdrawn from the side cut is adjusted so that the amount of tert-butanol contained in the side cut fraction becomes equal to that of tert-butanol fed into the fourth step.

3. The process according to claim 1, wherein the fraction from the side cut is withdrawn from any of a 28th to 30th plates in theoretical plate number from the top of the column.

* * * * *